United States Patent [19]

Gong

[11] Patent Number: 4,511,656

[45] Date of Patent: * Apr. 16, 1985

[54] DIRECT FERMENTATION OF D-XYLOSE TO ETHANOL BY A XYLOSE-FERMENTING YEAST MUTANT

[75] Inventor: Cheng-Shung Gong, West Lafayette, Ind.

[73] Assignee: Purdue Research Foundation, West Lafayette, Ind.

[ * ] Notice: The portion of the term of this patent subsequent to Jan. 11, 2000 has been disclaimed.

[21] Appl. No.: 376,731

[22] Filed: May 11, 1982

Related U.S. Application Data

[63] Continuation-in-part of Ser. No. 263,925, May 15, 1981, Pat. No. 4,368,268.

[51] Int. Cl.$^3$ ................................................ C12P 7/06
[52] U.S. Cl. .................................... 435/161; 435/163; 435/921; 435/942
[58] Field of Search ........................ 435/161, 163–165, 435/921, 924, 930, 940, 944

[56] References Cited

U.S. PATENT DOCUMENTS

| | | | |
|---|---|---|---|
| 1,857,429 | 5/1932 | Christensen | 435/163 X |
| 2,481,263 | 9/1949 | Tsuchiya et al. | 435/153 |
| 3,887,434 | 6/1975 | Frommer et al. | 435/172 X |
| 4,288,550 | 9/1981 | Ishida et al. | 435/940 X |
| 4,359,534 | 11/1982 | Kurtzman et al. | 435/161 |
| 4,368,268 | 1/1983 | Gong | 435/161 |

*Primary Examiner*—Robert Yoncoskie
*Attorney, Agent, or Firm*—Cushman, Darby & Cushman

[57] ABSTRACT

A process for obtaining ethanol directly from D-xylose through fermentation of D-xylose by xylose-fermenting yeast mutants. The process provides for obtaining ethanol from hemicellulose hydrolyzates through yeast fermentation of D-xylose to ethanol. In addition, a process for producing yeast mutants capable of utilizing D-xylose to ethanol in high yields is described. Furthermore, the process also provides for obtaining ethanol from a mixture of cellulose and hemicellulose hydrolyzates through yeast fermentation of D-glucose and D-xylose directly and simultaneously to ethanol.

23 Claims, 4 Drawing Figures

DIRECT FERMENTATION OF D-XYLOSE TO ETHANOL BY A XYLOSE-FERMENTING YEAST MUTANT

This application is a continuation-in-part of application Ser. No. 263,925, filed May 15, 1981, now U.S. Pat. No. 4,368,268.

BACKGROUND OF THE INVENTION

D-xylose, a five-carbon sugar, is a naturally occurring carbohydrate present in large quantities in a wide variety of plant materials. It often comprises over 60% of the recoverable sugars derived from hemicelluloses.

Numerous microorganisms such as bacteria and mycelial fungi are known to produce small amounts of ethanol and other products from D-xylose under fermentation conditions. These methods however, do not provide a means for the conversion of D-xylose to ethanol in high yields.

Many yeasts are capable of fermenting hexoses to ethanol anaerobically in high yields. However, no yeasts have been reported to ferment pentoses (or specifically D-xylose) to ethanol effectively, even though many yeasts are capable of both metabolizing pentoses aerobically, and in many cases, producing polyols (e.g., xylitol, and arabitol) as the metabolic by-products. Therefore, D-xylose, which is derived primarily from hemicellulosic materials, has been regarded as a nonfermentable sugar.

Several bacteria (e.g., clostridia) and mycelial fungi (e.g., Mucor spp., Rhizopus spp., Monilia spp., and Fusaria) are known to metabolize as well as ferment D-xylose to ethanol. However, for ethanol production from biomass, yeasts are preferred over bacteria and mycelial fungi. The yeast process for fermenting glucose to ethanol is a relatively simple and well-studied process. On the other hand, bacterial fermentation of D-xylose has not been satisfactory due to the low yield and the undesirable generation of organic acids (e.g., lactic acid) as fermentation products along with ethanol, as confirmed in U.S. Pat. No. 1,857,429. Mycelial fungal fermentation of D-xylose has not been satisfactory either, due to the slow-rate of fermentation and low-yield of ethanol.

The biological conversion of five-carbon sugars derived from hemicellulose to ethanol is important in order to fully utilize biomass so as to produce liquid fuels, especially in view of the fact that vast quantities of hemicellulosic materials are readily available. Unfortunately these materials have been greatly under-utilized due to the lack of the ability of proper organisms to convert D-xylose to ethanol efficiently.

Accordingly, it is the primary object of the present invention to provide a new process for the production of ethanol from D-xylose using novel xylose-fermenting yeast mutants.

It is also an object of the present invention to provide a means for obtaining yeast mutants which will utilize D-xylose to ethanol in high yields.

It is a further object of the present invention to provide a means for production of ethanol from both D-xylose and six-carbon sugars, simultaneously. These and other objects will be more apparent from the discussion below.

SUMMARY OF THE INVENTION

The present invention provides a process for producing ethanol from either D-xylose or D-xylose containing hemicellulose hydrolyzates or plant material hydrolyzates by fermentation which comprises inoculating D-xylose-fermenting yeast mutants capable of producing ethanol from D-xylose in over 50% and preferably over 80% yield. Moreover, the present invention also relates to inoculating the same yeast mutants capable of producing ethanol from glucose containing hydrolyzates and also from D-xylose containing hydrolyzates by fermenting both glucose and xylose, simultaneously. The product ethanol and yeast cells are then separated. The following discussion demonstrates the process of this invention wherein D-xylose and plant hydrolyzates are used as the starting fermentation substrates.

I. Production of Ethanol from D-xylose

As one embodiment of the present invention, there is provided a process for producing ethanol in a yield over 50%, and preferably over 80%, of theoretical value by aerobic or anaerobic fermentation of D-xylose by xylose fermenting yeast mutants. In carrying out such a process according to the present invention, yeast mutants that are created through either mutation mutagens (e.g., chemical or physical) may be employed. Also included within the scope of the "mutants" of the present invention are those strains obtained by protoplast fusions or recombinant DNA techniques. These mutation mutagens and the like are used to obtain mutants from a parent strain which has a limited ability (or in some instances no ability) in their unmutated state to ferment D-xylose to ethanol. For example *Candida diddensii*, *Candida utilis*, *Candida tropicalis*, *Candida parapsilosis*, *Candida subtropicalis*, *Pachysolen tannophilus*, *Saccharomyces diastaticus*, *Saccharomycopsis fibuligera*, *Saccharomyces cerevisiae*, *Saccharomyces uvarium*, *Schizosaccharomyces pombe*, *Kluyveromyces fragilis* and *Torula candida* and other D-xylose utilizing yeasts may be used as parent strains for the isolation of mutants through chemical, physical, biological mutation. Hybrids formation and DNA recombination techniques may also be employed.

A preferred method for obtaining the desired mutant strain involves initially isolating (randomly) a single colony of the parent strain which is then subjected to ultra-violet (uv) radiation to induce mutation. Thereafter, the resultant mutant strain is screened to isolate the specific colony or colonies having the best capability to utilize the D-xylose to produce ethanol.

By way of example, one may obtain a suitable mutant by selecting a parent strain having the ability to utilize D-xylose and isolating a single colony therefrom at random. A culture of that isolated colony is then prepared by growing same aerobically in a suitable media, such as a YM media, in an Eilenmeyer flask for 24 hours at 30° C. in an incubator shaker. The cells are then harvested by centrifugation and resuspended in sterile water at a density of about $1 \times 10^6$ cell/ml. The cells are then exposed to ultra-violet radiation so as to induce mutation. Suitably one may expose the cells to a UV lamp (e.g. an R-52 Mineralight ® lamp manufactured by Ultra-Violet Products, Inc.) positioned approximately six inches from the yeast cell for a period ranging from about 45 to about 150 seconds, and preferably about 100 seconds. The period of exposure will vary within these ranges depending on the particular strain.

Thus, a period of 100 seconds for Candida sp. has been found to be optimal, to obtain a 50% survival rate.

Subsequent to mutation, the resultant strain is screened to isolate the specific colony or colonies which will utilize D-xylose but not xylitol. This screening may be accomplished by plating the mutant cells on YM media agar plates with glucose as a carbon source. After 48 hours of incubation at 30° C., yeast colonies are separately plated on YM media with 1% D-xylose and 1% xylitol agar plate, respectively. Those mutant yeast colonies having the ability to grow on D-xylose and not xylitol are isolated and may be utilized for fermentation of D-xylose to ethanol in accordance with the present invention.

It should be noted that other means than UV radiation may be employed to induce mutation as noted above. The critical factors in obtaining suitable mutants are isolating a colony from a suitable parent strain and subsequent screening to isolate a mutant which will utilize D-xylose but not xylitol. It should be understood, that in screening the mutant strains, one should seek to isolate a specific colony or colonies which will utilize D-xylose but not such polyols as xylitol, arabitol etc. Thus, one may suitably utilize multiple screening plates in addition to or in lieu of the xylitol plate.

In producing ethanol from D-xylose, yeast mutants are inoculated into the medium containing appropriate growth nutrients (e.g., yeast extracts, malt extracts and peptone) and D-xylose as carbon and fermentation substrates. The D-xylose concentration can be varied in a wide range (1 to 40%), preferably 5 to 30%. The fermentation is conducted under aerobic or anaerobic conditions while maintaining the incubation at a temperature range of about 22° to 40° C., and preferably at about 30° C. After about 10 hours to 4 days (depending on sugar concentration, yeast density and other fermentation conditions), the D-xylose is consumed, and the ethanol so produced is accumulated.

II. Production of Ethanol from Sugarcane Bagasse hemicellulose Hydrolyzate

The hemicellulose hydrolyzate from sugarcane bagasse which contains 6.4% D-xylose, 1.8% L-arabinose, and 0.6% D-glucose was used as a fermentation substrate. Hemicellulose hydrolyzate was obtained by acid hydrolysis of bagasse. The pH was then adjusted to about 6 with the removal of undesired precipitants. To this hydrolyzate, D-xylose fermenting yeast mutant (e.g. Candida sp. XF-217) was inoculated ($2 \times 10^6$ cell/ml) and fermentation was carried out at 30° C. for 24 hrs. As a result, ethanol was produced in a high yield from D-xylose. The adjustment of pH mentioned is conducted by using calcium oxide and/or caustic soda. The pH range may vary from about 4 to about 8, and preferably is about 6. For further production of ethanol from additional hydrolyzates, the yeasts can be recycled and reused.

III. Production of Ethanol from Cellulose and Hemicellulose Hydrolyzate of Vegetable Materials The cellulose and hemicellulose hydrolyzates which contain higher amounts of D-glucose and D-xylose were also used as a fermentation substrate (i.e., 6.8% D-glucose, 5.3% D-xylose, and 0.8% L-arabinose). Fermentation was carried out as described above. As a result, ethanol was produced in the desired high yields.

Figure 1:
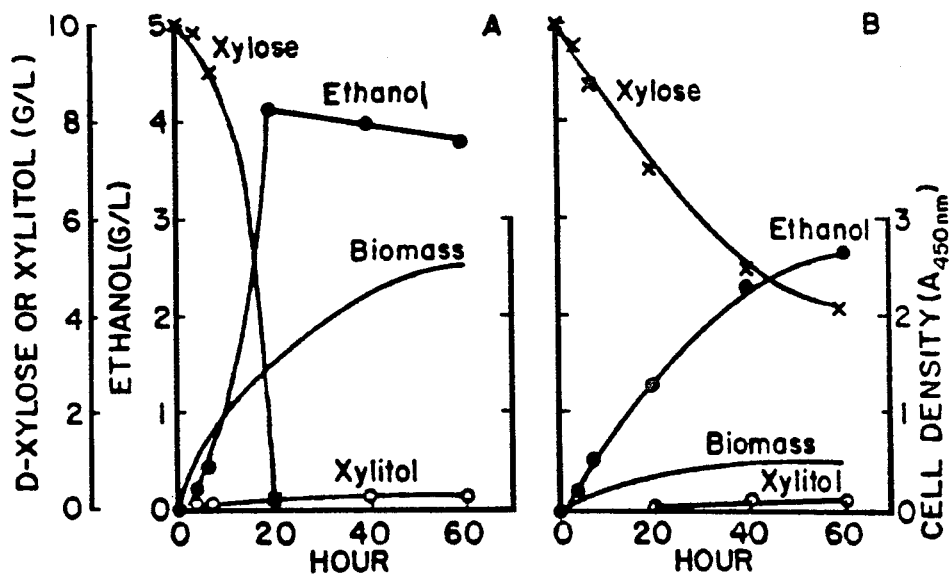
FIGS. 1 and 2 are graphs depicting cell growth and ethanol production from D-xylose (1% in FIG. 1 and 5% w/v in FIG. 2) by Candida sp. XF 217, graph A representing aerobic conditions and graph B anaerobic conditions.

The following examples are offered in order to more fully describe the present invention, but are not to be construed as limiting the scope thereof as departures may be made therefrom.

EXAMPLE 1 (Comparative)

Several existing yeast strains were examined for their ability to ferment D-xylose to ethanol. Those organisms so capable were inoculated into the culture liquid medium containing 0.3% Bacto-yeast extract, 0.3% Difco Malt-extract and 0.5% Bacto-peptone (referred to herein as YM medium) with 1% D-xylose and incubated with shaking at 30° C. for 24 hours. After incubation additional xylose was added (5%, wt/v) and the fermentation was carried out either under non-aerated or shaking conditions for 48 hrs at 30° C. The results of xylose fermentation are shown in Table 1 below.

The results indicate that most organisms tested utilized D-xylose aerobically, and some produced xylitol as a fermentation product, but none was able to produce high levels of ethanol. Under non-aerated condition, some yeasts utilized xylose, again with xylitol as fermentation product. However, only trace amounts of ethanol were produced. The results indicate that none of the yeast tested could effectively ferment xylose to ethanol. Earlier, Barnett (Barnett, J. A., Adv. Carbohydrate Chem. Biochem. 32: 125–234, 1976) surveyed 434 species of yeast, about half of the species were found to assimilate D-xylose aerobically and none are able to ferment D-xylose anaerobically to produce ethanol. This together with the results noted in Table 1 confirm that yeasts are not able to effectively ferment (i.e., yields greater than 50%) D-xylose to ethanol.

TABLE 1

Fermentation of D-Xylose by Yeasts

| Yeast | ATCC No. | Percent (%, w/v) Ethanol Produced | Xylitol |
|---|---|---|---|
| Candida diddensii | 20213 | 0.12 | 0.22 |
| Candida utilis | 9256 | 0.38 | 0.31 |
| Candida tropicalis | 1369 | 0.19 | 0.62 |
| Saccharomyces cerevisiae | 24860 | 0 | 0.17 |
| Saccharomyces cerevisiae | 24553 | 0 | 0.25 |
| Saccharomyces diastaticus | 28338 | 0.14 | 0.25 |
| Saccharomyces rouxii | 32901 | 0 | 0.35 |
| Saccharomyces saki | 26421 | 0 | 0.2 |
| Schizosaccharomyces pombe | 26192 | 0 | 0 |
| Haasenula polymorpha | 14754 | 0 | 0.2 |
| Pachysolen tannophilus | 32691 | 0.32 | 0.52 |
| Saccharomycopsis fibuligera | 32693 | 0.12 | 0.33 |
| Torula candida | 20214 | 0.12 | 0.17 |

Fermentation was carried out at 30° C. under fermentation conditions with shaking at 200 rpm.

The initial cell density was $2 \times 10^8$ cells per ml.

The initial sugar concentration was 5% (w/v) and incubation was for 48 hrs.

EXAMPLE 2

Yeast mutant strains isolated from Candida sp. XF217 (ATCC No. 20615) were examined for their ability to ferment D-xylose to ethanol aerobically or anaerobically. Organisms were inoculated into the liquid medium (YM medium) with 1% xylose and incubated with shaking at 30° C. for 24 hours. After initial incubation, an additional 5% xylose was added to the fermentation medium and the fermentation was carried out for 24 hours. At the end of the fermentation period, this broth was then centrifuged to remove the yeast cells. The ethanol produced was then analyzed and quantified by gas chromatography. As shown in Table 2 below, the mutant strains did ferment xylose to ethanol, while the parent strain is unable to produce ethanol from xylose in high yields.

TABLE 2

ETHANOL[a] PRODUCTION BY CANDIDA SP. AND XF 217[b]

| Sugars[c] | Candida sp. | | XF 217 | |
|---|---|---|---|---|
| | Aerobic | Anaerobic | Aerobic | Anaerobic |
| Glucose | 10.96 | 17.85 | 11.47 | 18.71 |
| Fructose | 11.33 | 17.02 | 13.71 | 17.55 |
| Xylose[d] | 2.27(42) | 1.52(17.3) | 11.63(.61) | 3.10(2.9) |
| L-Arabinose | 0.06 | 0.16 | 0.12 | 0.68 |
| Xylitol | 0.02 | 0.08 | 0.05 | 0.17 |
| Sucrose | 15.15 | 20.64 | 15.14 | 22.66 |
| Maltose | 10.58 | 14.53 | 6.87 | 9.44 |
| Lactose | 0.02 | 0.12 | 0.06 | 0.03 |

[a]Ethanol concentration was expressed as grams per liter (G/L).
[b]Incubation was carried out in flask cultures at 30° C., shaken at 200 rpm. The initial pH was 5.6, and the initial cell density was $1 \times 10^7$ cells per ml.
[c]The initial sugar concentration was 5% (w/v), and cultures were incubated for 24 hrs.
[d]Numbers in parentheses indicate grams/liter (w/v) xylitol produced.

Both Candida sp. and mutant strain XF 217 utilize D-glucose, D-fructose, D-xylose, L-arabinose, xylitol, sucrose and maltose as carbon and energy sources. When the yeasts from exponential growth phase were incubated with sugars under either growing (aerobic) or fermentative (anaerobic) conditions, ethanol was produced when the added sugars were D-glucose, D-fructose, sucrose or maltose. When D-xylose was the sugar used, Candida sp. produced xylitol, but XF 217 produced ethanol (Table 2). These results further indicate that the mutant strains of the present invention, such as XF 217, produce ethanol preferentially over xylitol production. In addition, the fermentation of D-xylose by the mutants such as XF 217 differs from the fermentation of hexose substrates, since oxygen must be available for enhanced ethanol production from D-xylose in XF 217.

Figure 2:
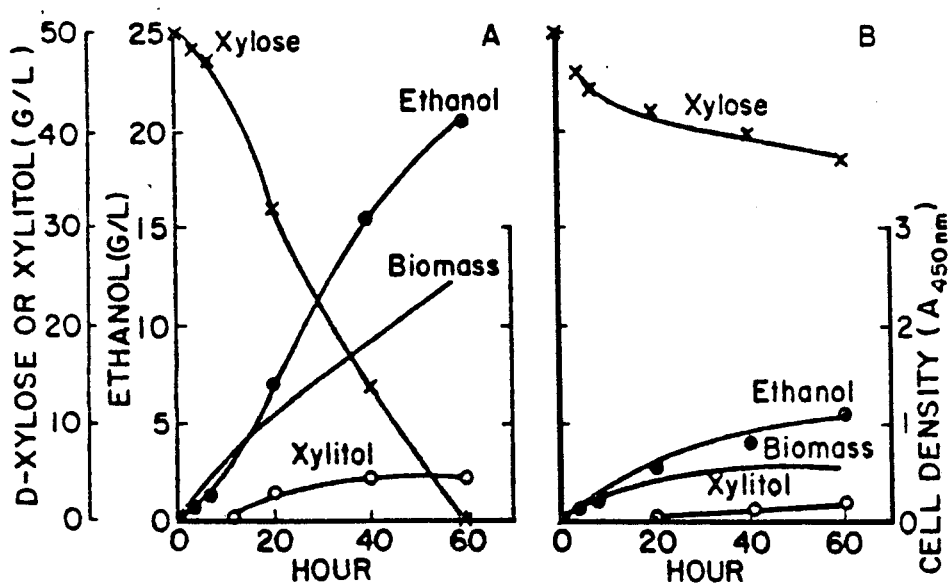

FIGS. 1 and 2 depict the growth and ethanol production by XF 217 when grown in 1% and 5% D-xylose as the sole energy and carbon source under aerated and fermentative conditions. The rates of growth and ethanol production are slower under fermentative conditions. These results indicate that oxygen is required for growth as well as the production of ethanol. Similar results were observed when higher concentration of D-xylose (%5 w/v) (FIG. 2) was used as substrate. Under these conditions, the ethanol yield was between 80% and 85% of the theoretical value.

EXAMPLE 3

Figure 3:
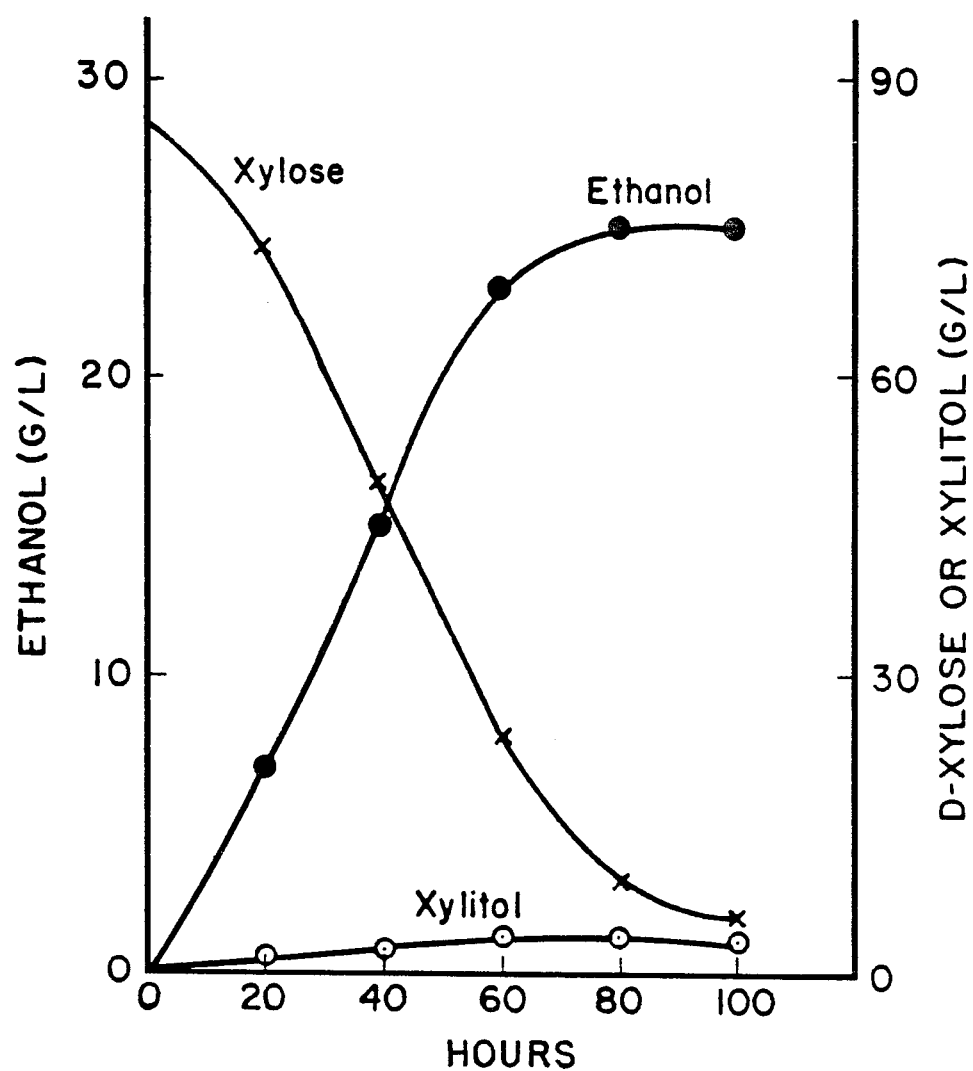
FIG. 3 is a graphic depiction of the ethanol production from aerobic fermentation of hemicellulose hydrolyzate by XF 217.
Figure 4:
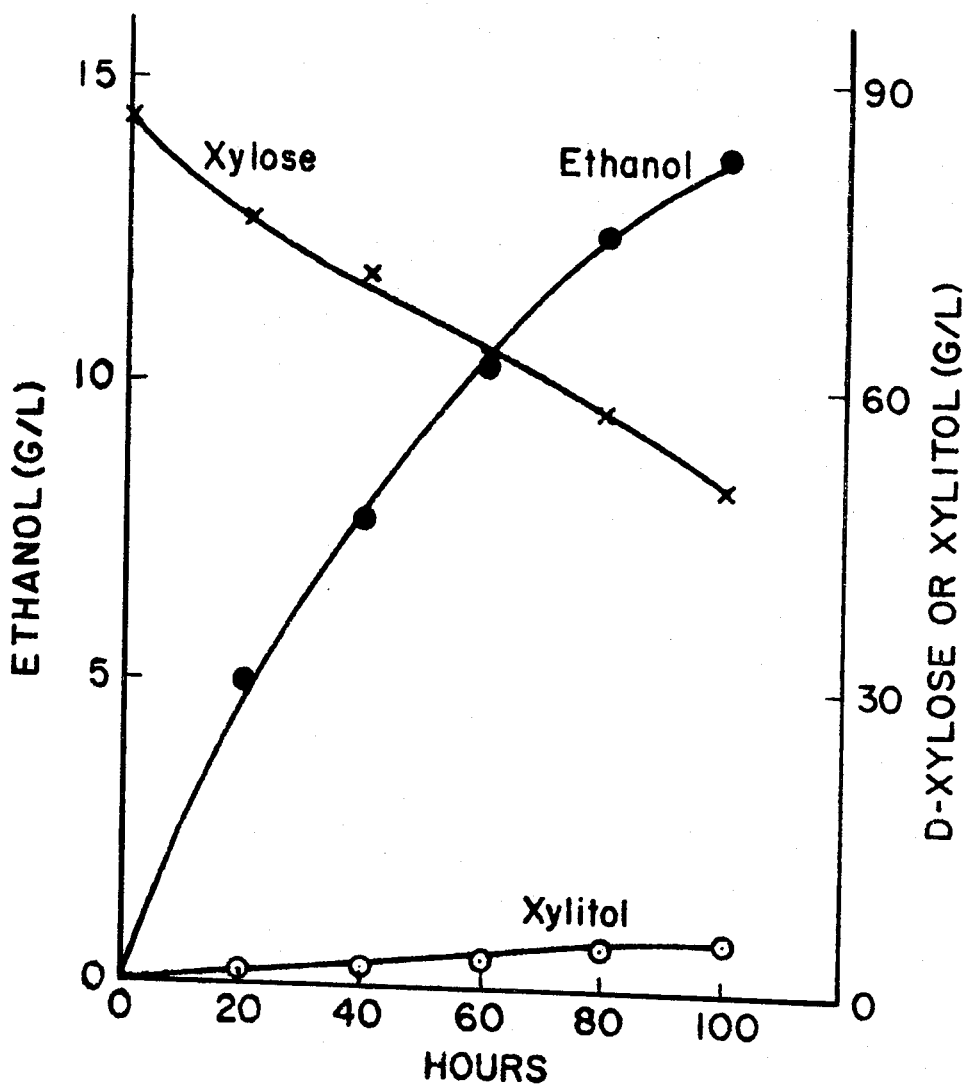
FIG. 4 represents the ethanol produced from the anaerobic fermentation of hemicellulose hydrolyzate by XF 217.

The mutant strain Candida sp. XF 217 (ATCC No. 20615) was inoculated into a liquid medium containing hemicellulose hydrolyzate, and incubated (in two separate preparations) both under aerobic conditions with shaking at 30° C. as well as under anaerobic conditions at 30° C. Samples were taken over a period of time (see FIGS. 3 and 4) and centrifuged to remove yeast cells. D-xylose concentration was measured by liquid chromatography, and the ethanol was measured by gas chromatography. Yeast cell growth was monitored by optical density at 450 nm and expressed as relative growth. The results shown in FIGS. 3 and 4 indicate that the XF 217 yeast is able to convert D-xylose contained in hemicellulose hydrolyzate to ethanol aerobically as well as anaerobically.

EXAMPLE 4

Yeast mutant strains isolated from S. cerivisiae were examined for their ability to ferment D-xylose to ethanol aerobically or anerobically. Organisms were inoculated into the liquid medium (YM medium) with 1% xylose and incubated with shaking at 30° C. for 24 hours. After initial incubation, an additional 5% xylose was added to the fermentation medium and the fermentation was carried out for 48 hours. At the end of the fermentation period, this broth was then centrifuged to remove yeast cells. The ethanol produced was then analyzed and quantified by gas chromatography. As shown in Table 3 below, the mutant strains ferment xylose to ethanol while the parent strain is unable to produce ethanol from xylose.

TABLE 3

AEROBIC AND ANAEROBIC CONVERSION OF D-XYLOSE TO ETHANOL[a] BY MUTANT STRAINS OF *SACCHAROMYCES CEREVISIAE*[b]

| Strain | Ethanol (%, w/v) | |
|---|---|---|
| | Aerobic | Anaerobic |
| SC (parent strain ATCC No. 24553) | 0 | 0 |
| SCXF8 | 1.17 | 0.82 |
| SCXF48 | 1.41 | 0.94 |
| SCXF69 | 1.05 | 1.17 |
| SCXF70 | 0.94 | 0.94 |
| SCXF76 | 1.05 | 1.29 |
| SCXF102 | 1.41 | 1.05 |
| SCXF108 | 0.59 | 1.17 |
| SCXF118 | 1.29 | 1.05 |
| SCXF120 | 0.94 | 0.94 |
| SCXF138 (ATCC No 20618) | 1.41 | 1.29 |

[a]Ethanol concentration was expressed as percent (w/v).
[b]Incubation was carried out in flask culture at 30° C. shaken at 200 rpm. The initial pH was 5.6, and the initial cell density was $2 \times 10^7$ cells per ml. The initial D-xylose concentration was 5% (w/v), and cultures were incubated for 48 hrs.

The use of a single organism such as yeast to convert both hexose and pentose to ethanol in high yields would be ideal. The present invention demonstrates that the D-xylose fermenting yeast strains such as XF 217, SCXF 138 and the like can be used to achieve this goal.

The invention having been thus described, it will be appreciated that various departures can be made therefrom without departing from the scope thereof. Furthermore, the invention may comprise, consist, and/or consist essentially of the hereinbefore recited materials and steps.

What is claimed is:

1. A process for the direct fermentation of D-xylose to ethanol which comprises inoculating a medium comprising growth nurients and D-xylose with a yeast mutant having an ability to ferment D-xylose to ethanol with a bioconversion yield of at least 50%, permitting the inoculated medium to ferment for a period of time sufficient to achieve a conversion of D-xylose to ethanol of at least 50% and recovering the ethanol so produced as product, said mutant being obtained from a parent yeast strain selected from the group consisting of Candida sp. and *Saccharomyces cerevisiae.*

2. The process of claim 1 wherein the conversion of D-xylose to ethanol is at least 80%.

3. A process according to claim 1 wherein the parent yeast strain is Candida sp.

4. A process according to claim 1 wherein the yeast mutant is Candida sp. XF 217.

5. A process according to claim 1 wherein the parent strain is *Saccharomyces cerevisiae.*

6. A process according to claim 1 wherein the yeast mutant is *Saccharomyces cerevisiae* SCXF 138.

7. A process according to claim 1 wherein the initial concentration of D-xylose in said medium ranges from 1 to about 40 percent on a weight/volume basis.

8. A process according to claim 7 wherein said initial concentration ranges from about 5 to 30 percent.

9. A process according to claim 1 wherein fermentation is carried out at a temperature ranging from about 22° to about 40° C.

10. A process according to claim 9 wherein said temperature is about 30° C.

11. A process according to claim 1 wherein fermentation is carried out at a pH ranging from about 4 to about 8.

12. A process according to claim 11 wherein said pH is about 6.

13. A process according to claim 1 wherein fermentation is carried out under aerobic conditions.

14. A process according to claim 1 wherein fermentation is carried out under anaerobic conditions.

15. A process according to claim 1 wherein the D-xylose is contained in hemicellulose hydrolyzate.

16. A process according to claim 1 wherein said medium also contains cellulose hydrolyzate material.

17. A process for the direct fermentation of D-xylose to ethanol which comprises inoculating a medium comprising growth nutrients and D-xylose in an amount of from 1 to about 40% by weight/volume of said medium with a yeast mutant having an ability to ferment D-xylose to ethanol with a bioconversion yield of at least 50%, fermenting the inoculated medium at a temperature ranging from about 22° to about 40° C. and a pH ranging from about 4 to about 8 for a period of time sufficient to achieve at least a 50% conversion of the D-xylose to ethanol, and recovering the ethanol so produced as product, said mutant being obtained from a parent yeast strain selected from the group consisting of Candida sp. and *Saccharomyces cerevisiae.*

18. A process according to claim 17 wherein the temperature is about 30° C. and pH about 6.

19. A process for the production of ethanol directly and simultaneously from D-glucose and D-xylose which comprises inoculating a medium comprising growth nutrients, D-glucose and D-xylose with a yeast mutant having an ability to ferment D-glucose and D-xylose to ethanol with a bioconversion yield of at least 50%, fermenting the inoculated medium for a period of time sufficient to achieve a conversion of D-xylose to ethanol of at least 50% and recovering the ethanol so produced as product, said mutant being obtained from a parent yeast strain selected from the group consisting of Candida sp. and *Saccharomyces cerevisiae.*

20. A process according to claim 19 wherein the D-glucose and D-xylose are obtained from cellulose and hemicellulose hydrolyzate.

21. A process according to claim 17 or 19 wherein said yeast mutant is Candida sp. XF217.

22. A culture consisting essentially of a mutant strain Candida sp. XF 217.

23. A culture consisting essentially of a mutant strain *Saccharomyces cerevisiae* SCXF 138.

* * * * *